United States Patent [19]

Lecoufle et al.

[11] Patent Number: Plant 6,510

[45] Date of Patent: Jan. 3, 1989

[54] PHALAENOPSIS PLANT NAMED VELMER

[75] Inventors: Maurice Lecoufle, Boissy-st-Leger; Michel Vacherot, Roquebrune-Sur-Argens, both of France

[73] Assignee: Orchidees les Petits Fils et Fils de Vacherot & Lecoufle, Boissy-st-Leger, France

[21] Appl. No.: 938,959

[22] Filed: Dec. 8, 1986 (Under 37 CFR 1.47)

[30] Foreign Application Priority Data

Aug. 4, 1986 [FR] France ..... 06212

[51] Int. Cl.[4] ..... A01H 5/00

[52] U.S. Cl. ..... Plt./68

[58] Field of Search ..... Plt. 68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Phalaenopsis plant named Velmer particularly characterized by its round flower shape, heavy substance, superior lasting quality of the flower when cut, superior vigor and growth habit, and by its white to yellow labellum, yellow-orange callus and generally brown streaking on the callus parts of the labellum.

2 Drawing Sheets

The present invention comprises a new and distinct cultivar of orchid, botanically known as Phalaenopsis, and hereinafter referred to by the cultivar name Velmer.

Velmer is a product of a planned breeding program which had the objective of creating new orchid cultivars having floriferous white flowers with a good round shape of heavy substance, superior lasting quality of the flowers when cut, superior vigor to provide fast growth, and a cultivar having such characteristics so as to provide superior breeding potential.

Velmer was originated from a hybridization made by Maurice Lecoufle and Michel Vacherot in a controlled breeding program in Boissy-st-Leger (Val de Marne), France in 1963. The female parent was the Phalaenopsis cultivar Lachesis (Fanchette×Cendrillon). The male parent of Velmer was the Phalaenopsis cultivar Ramona (Thomas Tucker×Mem. Nasu Tomogushi). The entire progeny of this hybridization was identified by the name of Phalaenopsis Henriette Lecoufle.

Velmer was discovered and selected as one flowering plant within the Henriette Lecoufle progeny by Maurice Lecoufle in June 1967 in a controlled environment in Boissy-st-Leger, France.

The first act of asexual reproduction of Velmer was accomplished when stem propagations and meristems were taken by applicants from the initial selection on Feb. 25, 1972 in a controlled environment in Boissy-st-Leger, France. Horticultural examination of selected units initiated in March of 1975 has demonstrated that the combination of characteristics as herein disclosed for Velmer are firmly fixed and are retained through successive generations of asexual reproduction.

The phenotype is well fixed and easily recognizable in different environment and conditions, although it may vary in size and in perfection of shape with variations such as temperature, light intensity and day length. The following observations, measurements, and comparisons describe plants grown in Boissy-st-Leger, France under conditions which approximate those generally used in commercial practice.

The traits described below have been repeatedly observed and are determined to be basic characteristics of Velmer which in combination distinguish this orchid as a new and distinct cultivar.

The accompanying color photographic drawings show typical plant and flower characteristics of Velmer, with colors being as true as possible with illustrations of this type. Sheet 1 comprises a color photograph in front elevational view showing the foliage and numerous flowers of Velmer. Sheet 2 comprises a color photograph showing in enlarged form the unique flower color of Velmer.

In the following description, color references are made to The Royal Horticultural Society Colour Chart. The color values were determined at approximately 3:00 p.m. on Sept. 15, 1986 on a clear day but with no direction sunlight at Boissy-st-Leger, France.

THE PLANT

Origin: Seedling.

Parentage:

*Seed parent.*—Phalaenopsis, Ramat., Lachesis.

*Pollen parent.*—Phalaenopsis, Ramat., Ramona.

Classification:

*Botanical.*—Phalaenopsis hybrid.

*Commercial.*—Phalaenopsis mericlone.

Form: Herbaceous plant.

Height (mature): 95 to 120 cm.

Growth habit: Monopodial.

Rizone: None.

Flowers per stem: From 1 to 25 (begins to flower when small).

Foliage:

*Quantity.*—2 to 5 pairs of alternately opposed leaves.

*Size of leaf.*—length, 25 to 30 cm; width, 13 to 15 cm.

*Shape of leaf.*—oval, fleshy, hard.

*Texture.*—strong substance, thickness, 2 to 3 mm.

*Color.*—purplish tinge on dark green. Primary color green 137A.

FLOWERS

Blooming habit: Recurrent.

Size (mature diameter): 105 to 118 mm.

Shape: Round.

Color: The primary sepal color when the flower is mature is 155D. The attachment of the labellum is 158C terminated by small bars of 166B; the lower lobes and the extending points of the lower labellum are 12C, with two primary and other smaller streaks of 166A in the throat; the triangular callus in the middle of the labellum is primarily 16A, with small spots of two V-shaped bars at the base being 166B; at the lower edges of the labellum, as seen in the enclosed photograph, there is a slight darkening of 164A; the under surface of the sepals is 155D, touched with 186D on the top of the dorsal sepal and at the base of the lower sepals. The peduncles are 193A–D at the base and middle, and 155A–B near the flower.

Texture: Lustreless.

Appearance: Crystalline and shiny.

Disease resistance: No particular sensibility to disease.

Fragrance: None.

Lasting quality: 6 to 10 weeks.

Petals:

*Width.*—72 mm.

*Length.*—56 mm.

Dorsal sepals:

*Width.*—40 mm.

*Length.*—56 mm.

Lateral sepals:

*Width.*—34 mm.

*Length.*—56 mm.

We claim:

1. A new and distinct Phalaenopsis plant named Velmer, as described and illustrated, and particularly characterized by its round flower shape, heavy substance, superior lasting quality of the flower when cut, superior vigor and growth habit, and by its white to yellow labellum, yellow-orange callus and generally brown streaking on the callus parts of the labellum.

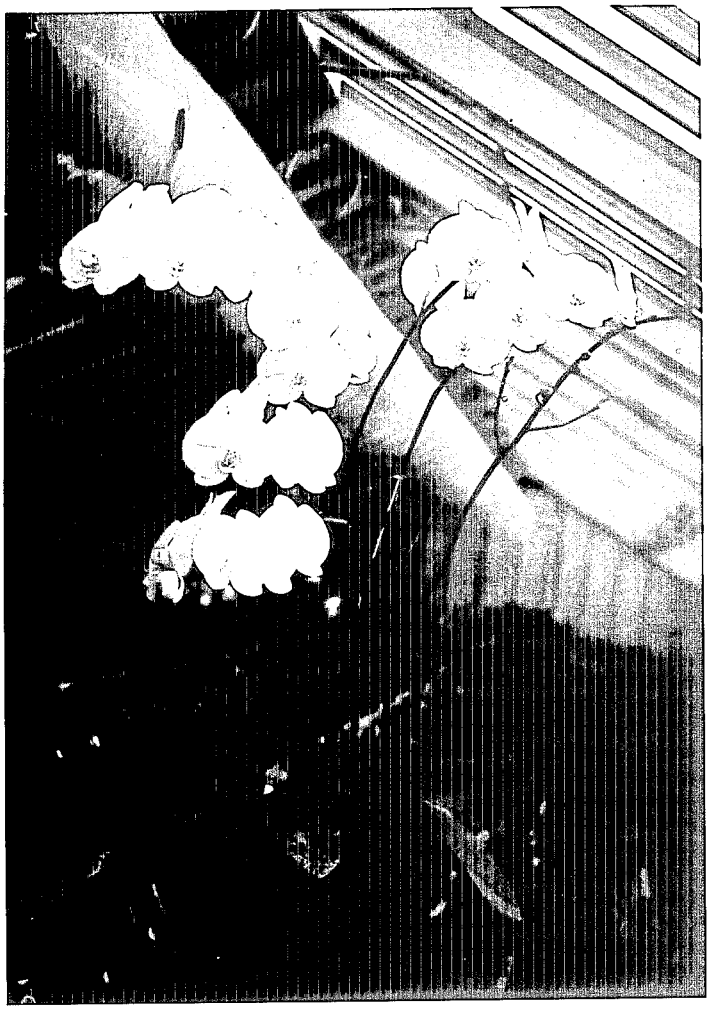

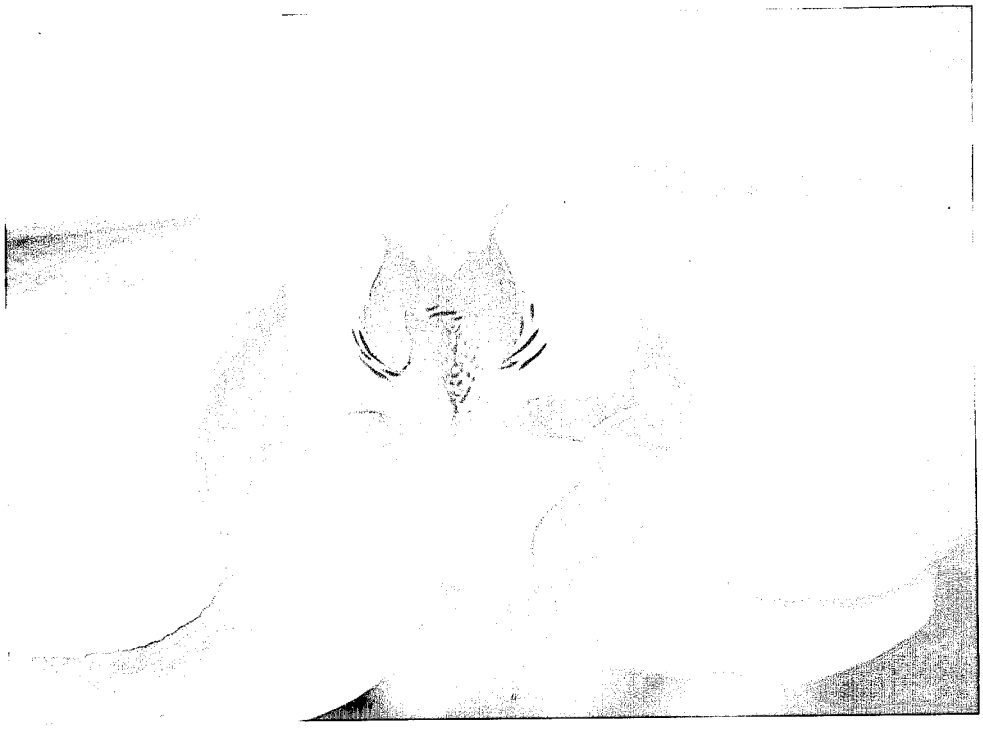

* * * * *